US006306075B1

(12) United States Patent
Shadduck

(10) Patent No.: US 6,306,075 B1
(45) Date of Patent: Oct. 23, 2001

(54) NON-CONTACT MAGNETORESONANT IMPLANT SYSTEM AND TECHNIQUES FOR PERIODIC CORNEAL RE-SHAPING

(76) Inventor: John H. Shadduck, 1490 Vistazo West St., Tiburon, CA (US) 94920

( * ) Notice: Subject to any disclaimer, the term of this patent is extended or adjusted under 35 U.S.C. 154(b) by 0 days.

(21) Appl. No.: 09/473,731

(22) Filed: Dec. 27, 1999

Related U.S. Application Data

(63) Continuation of application No. 09/128,056, filed on Aug. 3, 1998, now Pat. No. 6,006,756.
(51) Int. Cl.[7] .......................... A61B 17/52; A61B 17/38; A61B 17/36
(52) U.S. Cl. ................................. 600/12; 600/9; 606/5; 606/27; 607/53
(58) Field of Search .......................... 600/9, 12; 606/166, 606/5, 34, 27, 41; 607/53, 54

(56) References Cited

U.S. PATENT DOCUMENTS

| 3,653,385 | * | 4/1972 | Burton | 606/27 |
| 4,381,007 | * | 4/1983 | Doss | 606/27 |
| 5,465,737 | * | 11/1995 | Schachar | 623/4 |
| 5,533,999 | * | 7/1996 | Hood et al. | 606/4 |
| 5,766,171 | * | 6/1998 | Silvestrini | 606/49 |
| 6,006,756 | * | 12/1999 | Shadduck | 606/5 |
| 6,074,385 | * | 6/2000 | Klopotek | 606/27 |

* cited by examiner

Primary Examiner—Eric F. Winakur
Assistant Examiner—Navin Natnithithadha
(74) Attorney, Agent, or Firm—James F. Hann; Haynes Beffel & Wolfeld LLP

(57) ABSTRACT

A system and technique called magnetoresonant induction of an intrastromal implant that is adapted for corneal re-shaping. The technique is utilized to correct mild to high hyperopia and presbyopia by steepening the anterior corneal curvature in a single treatment, or in periodic treatments over the lifetime of the patient. The system comprises a combination of components including (i) at least one implantable magnetoresonant intrastromal segment, and (ii) an oscillating magnetic field generator together with a dosimetry control system including at least one emitter body adapted for positioning proximate to the patient's eye and intrastromal implant. The system can deliver thermal effects to appropriate stromal lamellae by non-contact inductive heating of the implant which in turn contracts or compresses stromal collagen fibrils into a circumferenitial cinch about an anterior layer of the cornea and steepens the anterior corneal curvature. A dosimetry control system controls the power level and duration of exposure of the oscillating magnetic field(s) and may be combined with intraoperative corneal topography. The system can be adapted for non-contact energy delivery to selected locations in other body structures in the interior of a patient's body.

13 Claims, 13 Drawing Sheets

NON-CONTACT MAGNETORESONANT IMPLANT SYSTEM AND TECHNIQUES FOR PERIODIC CORNEAL RE-SHAPING

CROSS-REFERENCE TO RELATED APPILICATIONS

This application is a continuation of U.S. patent application Ser. No. 09/128,056 filed Aug. 3, 1998 now U.S. Pat. No. 6,006,756.

BACKGROUND OF THE INVENTION

1. Field of the Invention

The present invention relates to devices and techniques for non-contact thermal treatment of a patient's cornea for altering anterior corneal curvature to correct refractive disorders, and more particularly, to implantable intrastromal segments that may be elevated in temperature by magnetic induction to cause lesions in, or shrinkage of, the Bowmnan's layer and/or stromal lamellae to increase corneal steepness in hyperopic or presbyopic refractive treatments.

2. Description of the Related Art

Refractive disorders of the eye result from the inability of the eye's optic system, consisting of the dome-shaped cornea and the crystalline lens just behind it, to properly focus images on the retina, the nerve layer at the back of the eye. Approximately 80 percent of the refracting power of a human eye is within the cornea. When the cornea is misshaped, or the eye is too long or too short along its optical axis, or when the lens of the eye does not function normally, a refractive error occurs. Refractive errors generally include hyperopia, myopia, presbyopia and astigmatisms. Hyperopia is a refractive error that causes poor close-up vision, and is caused by a flattened cornea or by a shortened eye that focuses images beyond the retina (see FIG. 1A). Myopia is the opposite and causes poor distance vision, and is characterized by an elongate eye or steepened corneal shape. This condition causes distant images to focus in front of the retina rather than directly on it (see FIG. 1B). Presbyopia results from aging and is a form of farsightedness caused by diminished ability of the lens to elastically change to refract light. Astigmatism is a condition which causes blurred vision for both near and far objects. In an astigmatic patient, the cornea may be shaped like the back of a spoon rather than having a spherical shape. Such an asymmetric corneal shape creates different retinal focal points. Hence, instead of images focusing on the retina, the images focus on a number of points around the retina resulting in a blurred image.

The optimal shape for a cornea is that of a perfect sphere assuming that axis of the eye is normal relative to the other eye. Glasses and contact lenses correct refractive errors by refracting (bending) light before it reaches the cornet and is transmitted through the lens, in other words, changing the angle at which light enters the cornea.

Several types of surgical procedures have been developed to correct refractive disorders such as myopia, hyperopia and astigmatisms by changing the shape of the cornea. For example, laser procedures can reshape the patient's cornea to some extent to a corrected more spherical shape, the most common procedures being laser in-situ keratomileusis (LASIK) and laser photorefractive keratectomy (PRK). LASIK and PRK correct vision by recontouring the anterior layers of the cornea by means of surface ablation with a laser.

It is useful to provide a description of the anatomy of the patient's eye. FIG. 1C depicts patient's eye 5 which comprises a system of cornea 6 and lens 3 which focuses light on the retina indicated at 4 which is at the back of the substantially spherical body defined by sclera 7. The anterior chamber 8 (and aqueous 9a therein) is separated from the vitreous body 9b by lens 3. Thus, cornea 6 forms the anterior wall of chamber 8 and also acts as a lens element. The cornea 6 is a smoothly curved transparent structure which has a smaller radius of curvature than the opaque sclera 7 and bulges from the smooth outer spherical surface of the eye. Refractive errors occur when the cornea and lens do not focus incoming light on retina 4.

The cornea 6 is uniquely structured to transmit light into the eye. The primary structure of the cornea is the stroma, which comprises approximately 90 percent of the cornea's thickness. The stroma is comprised of lamellae which lie in flat sheets and extend from limbus to limbus. Each lamella (layer or sheet) consists of strong, parallel collagen fibrils which are maintained in a regularly spaced hexanal separation by a ground substance or GAGs (for glycoaminoglucans, also called a glycolprotein and mucopolysaccharide matrix). Between the lamellae are keratocytes layers (the fibroblasts), the constitutive cells of the cornea which produce the GAGs and support synthesis of collagen. It is well known that the elongate stromal collagen fibrils may be longitudinally contracted by application of heat to temperatures above about 60° to 65° C. See, e.g., U.S. Pat. No. 4,461,294 issued to Baron; U.S. Pat. No. 4,976,709 issued to Sand; U.S. Pat. No. 4,326,529 and U.S. Pat. No. 4,381,007 issued to Doss; and U.S. Pat. No. 5,533,999 issued to Hood.

SUMMARY OF THE INVENTION

The invention is termed herein a $MI^3$ system and technique (magnetoresonant induction of intrastromal implant) for re-shaping a pattient's corneal by contracting collagen fibrils to form a circumferential "cinch" or "ring" around the cornea. The $MI^3$ system and technique may be utilized to correct mild to high hyperopia and presbyopia by steepening the anterior corneal curvature in a single treatment, or in periodic treatments over the lifetime of the patient.

The $MI^3$ system is a combination including (i) at least one magnetoresonant implantable intrastromal segment, and (ii) an oscillating magnetic field generator together with a dosimetry control system. At least one emitter is provided and is adapted for positioning proximate to the patient's eye and the intrastromal implant. Thus, the $MI^3$ system is adapted to deliver thermal effects to appropriate stromal lamellae by non-contact inductive heating of the implant which in turn contracts or compresses stromal collagen fibrils into a circumferential cinch within an anterior layer of the cornea to steepen the anterior corneal curvature. The dosimetry control system controls the power level and duration of exposure of the oscillating magnetic field(s).

In general, the present invention advantageously provides a system that will require less than a few minutes of procedure time to correct corneal curvature in an office setting, once the magnetoresonant implants are in place.

The invention advantageously provides a "norn-contact" system of delivering thermal energy to collagenous tissues to correct corneal curvature in hyperopic or presbyopic patients.

The invention advantageously provides a system for correcting hyperopic or presbyopic errors in periodic treatments over the lifetime of the patient.

The present invention provides a system that can correct vision without invasion of the patient's visual axis.

The present invention advantageously provides a system having an arrangement of a plurality of N oscillating magnetic field emitters positioned about a central axis of the system and the patient's optical axis to allow such axes to be free for concurrent adjunctive diagnostic or therapeutic systems, such as intraoperaive corneal topography.

The invention advantageously provides a system having N emitters that allows opposing emitters to direct oscillating magnetic fields at opposing quadrants of the cornea and implants therein simultaneously to provide a substantial symmetry of treatment.

The invention further advantageously provides a system having N emitters that allows each of the N applicators to direct oscillating magnetic fields at opposing quadrants of the cornea at independent power levels to provide a refiled method of energy delivery to spaced apart implants portions for treatments of astigmaitisnm.

The invention advantageously provides a system of delivering thermal energy to the Bowman's layer or stroma without ablating epithelial layers.

The invention advantageously provides a device having a system of delivering thermal energy to a mid-stromal regions without the high peak temperatures associated with pulsed lasers.

The invention advantageously provides a system for contracting stromal collagen while using a heat-sink contact lens for simultaneously lowering the temperature of the anterior surface of the cornea sink to protect the corneal epithelium.

Additional features and advantages of the device and method of the present invention will be understood from the following description of the preferred embodiments, which description should be taken in conjunction with the accompanying drawings.

BRIEF DESCRIPTION OF THE DRAWINIGS

Figure 7A:
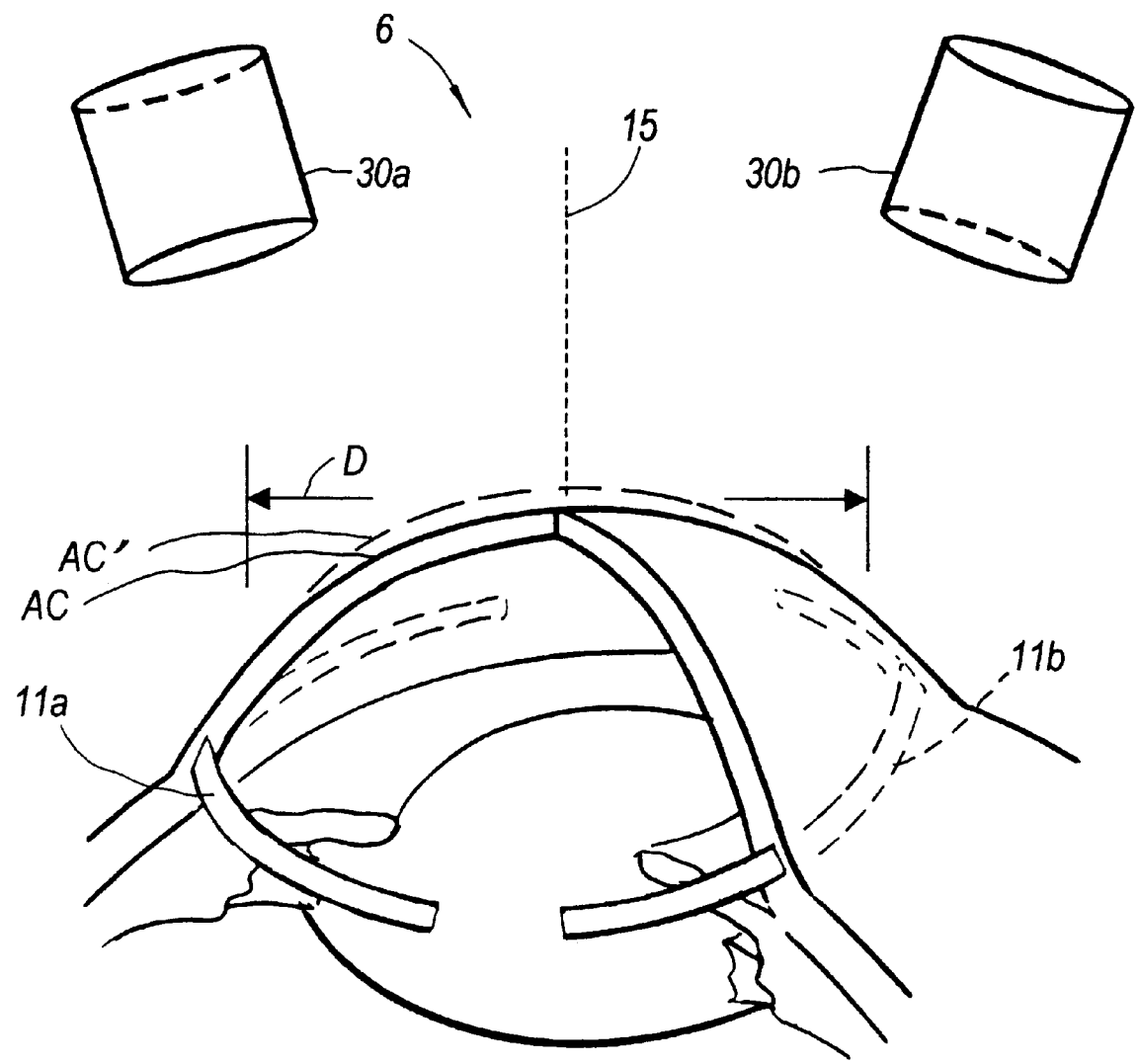
Figure 7B:
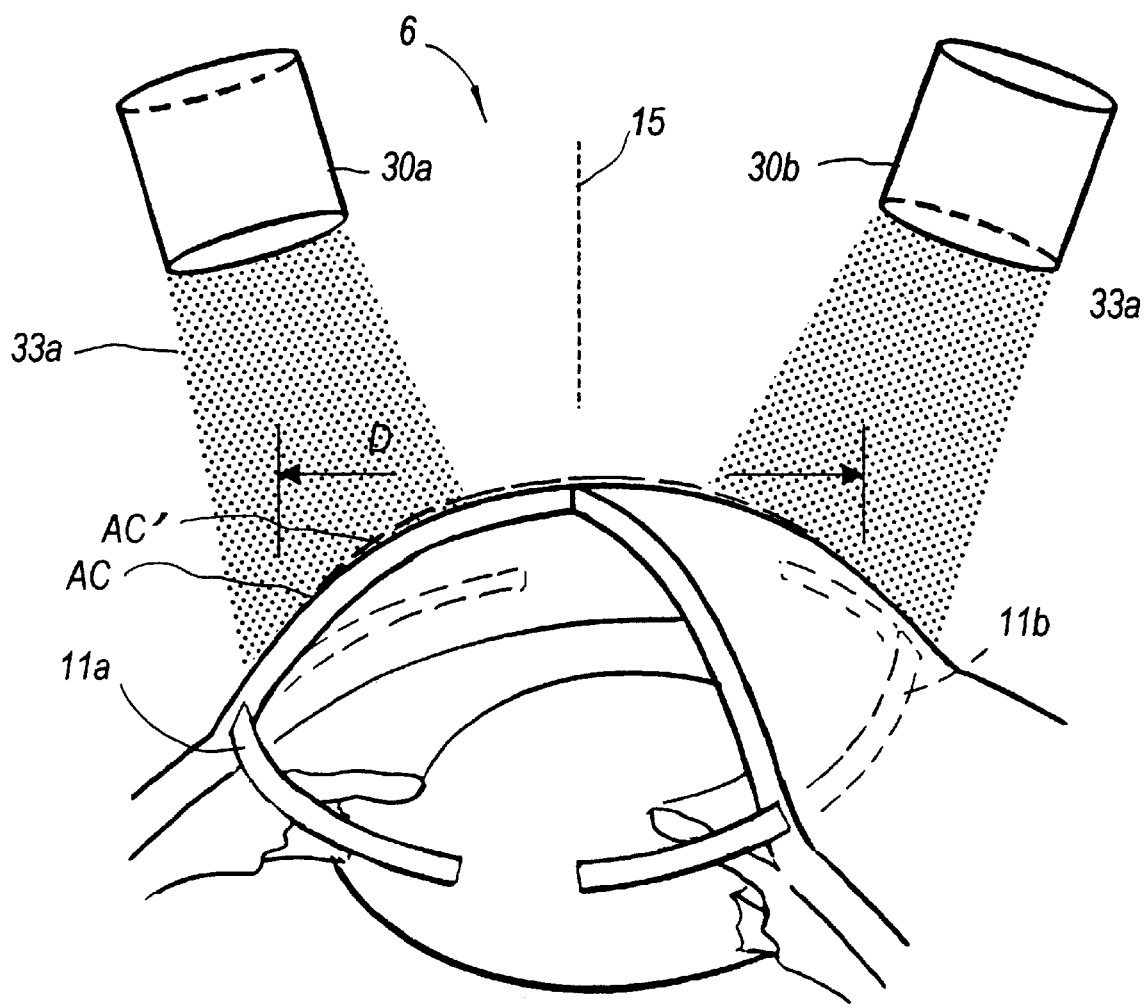

FIGS. 7A–7B are partial sectional representations of a patient's cornea depicting a manner of utilizing the system in performing a mtthcd of the invention to alter the shape of the patients' cornea; FIG. 7A showing the cornea and magnetically responsive implant at the initiation of energy delivery; FIG. 7B showing the cornea having a steepened shape after magneto-inductive heating of the implant which denatures and contracts intrastromal collagen lamellae creating a circumferential cinch around the cornea.

Figure 8A:
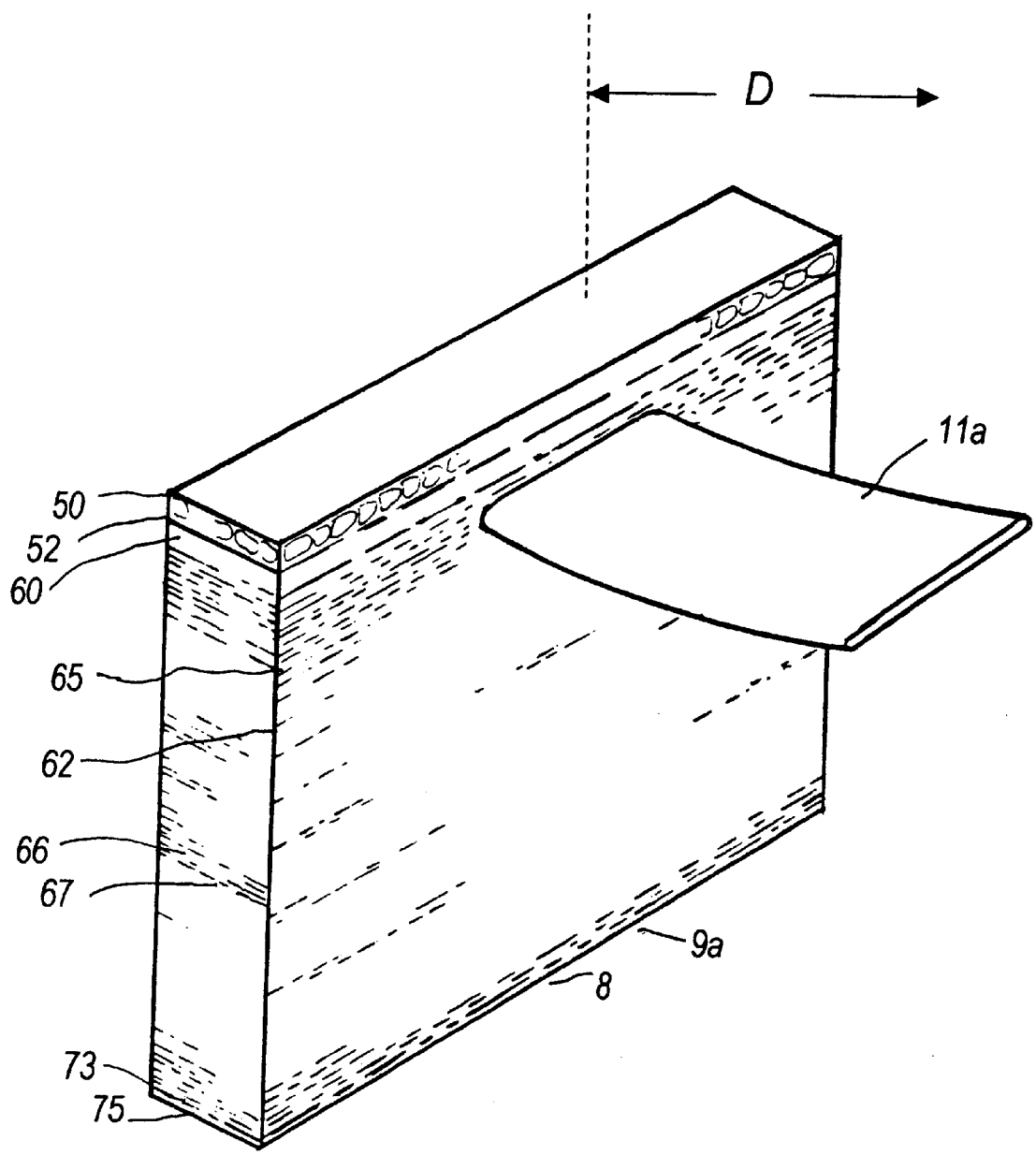
Figure 8B:
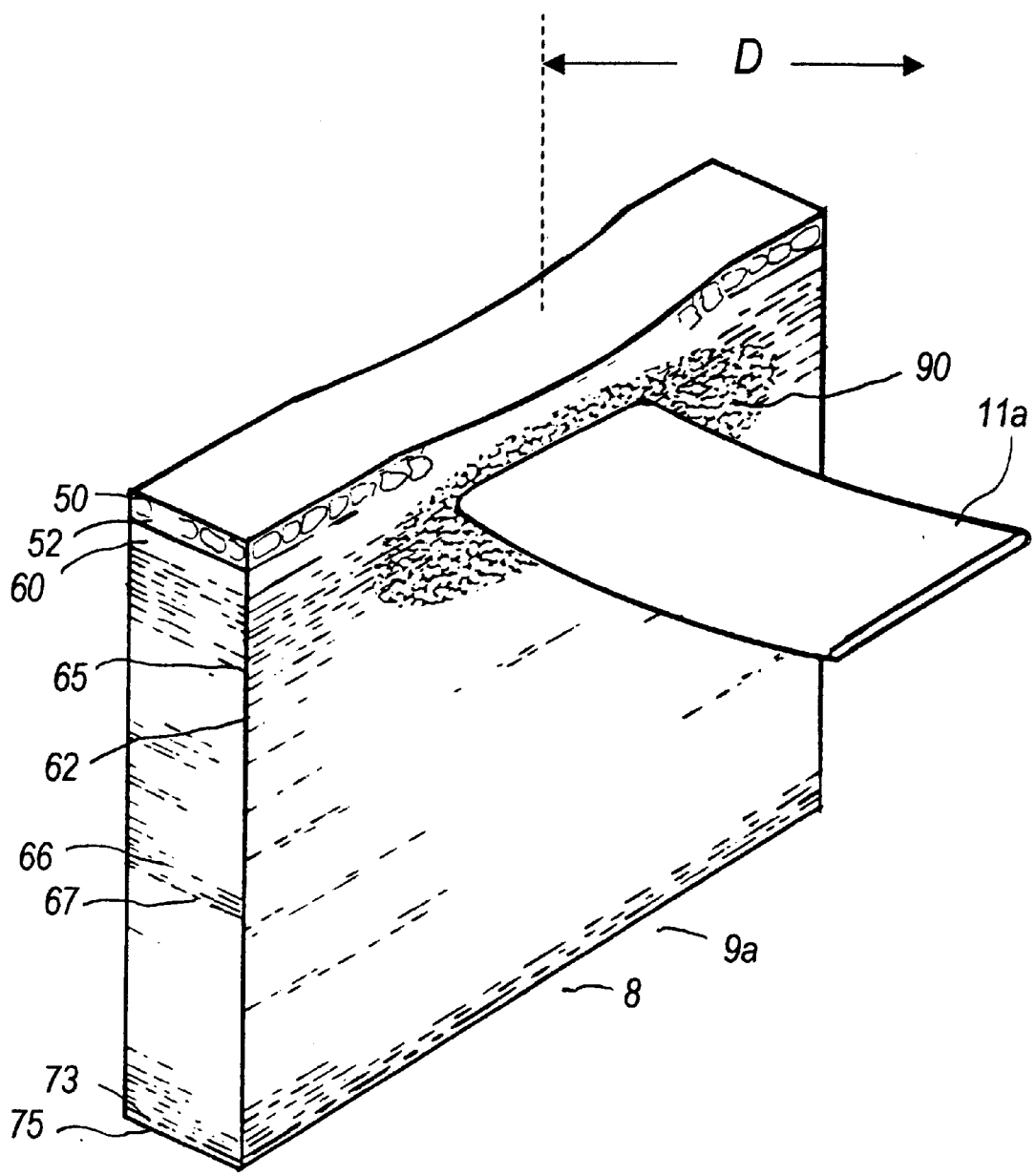

FIGS. 8A–8B are enlarged sectional views of the intrastromal implant and cornea of FIGS. 7A and 7B.

Figure 9:
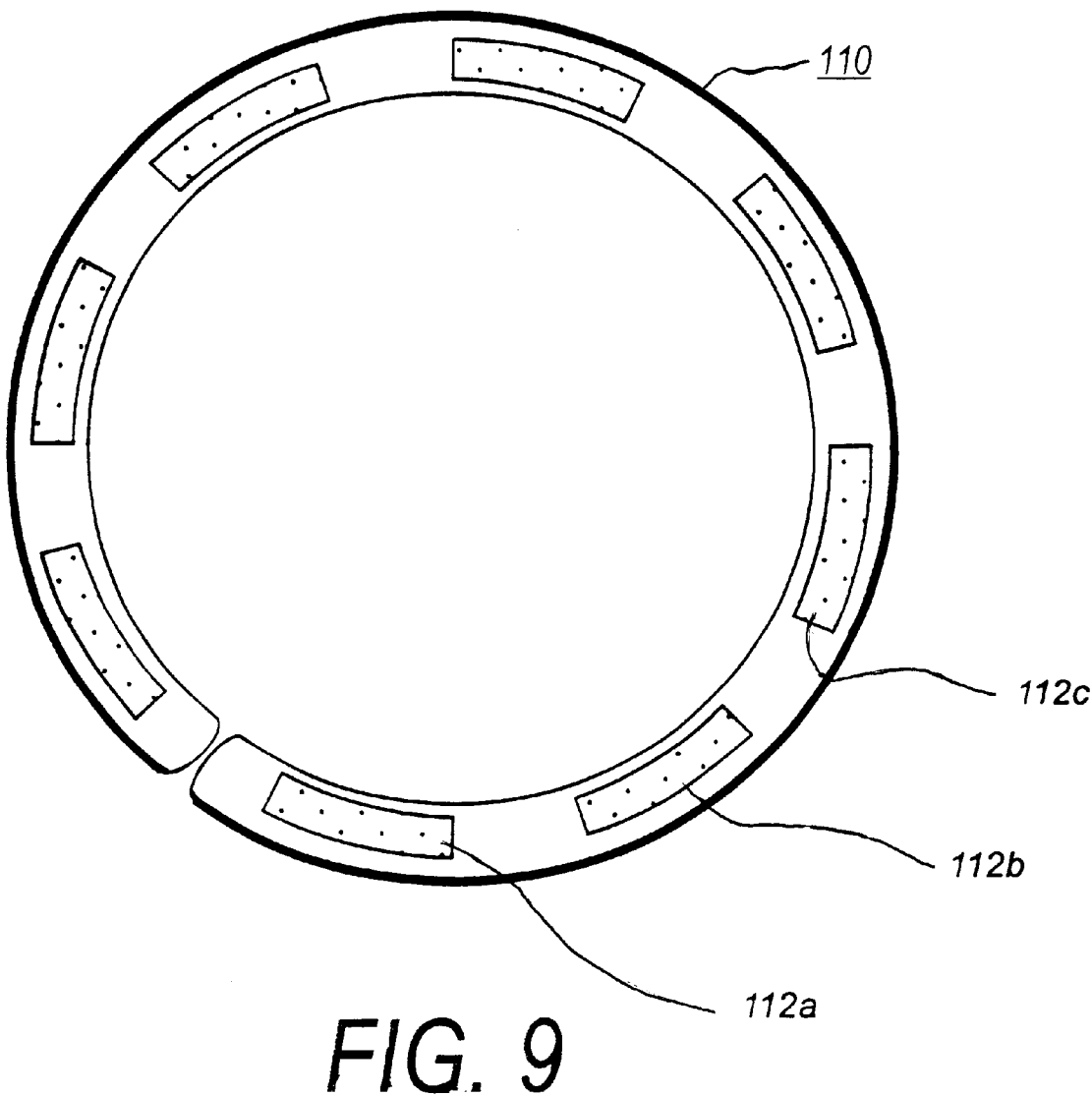

FIG. 9 is a plan view of a Type "B" embodiment of a magnetically responsive intrastromal implant.

Figure 10:
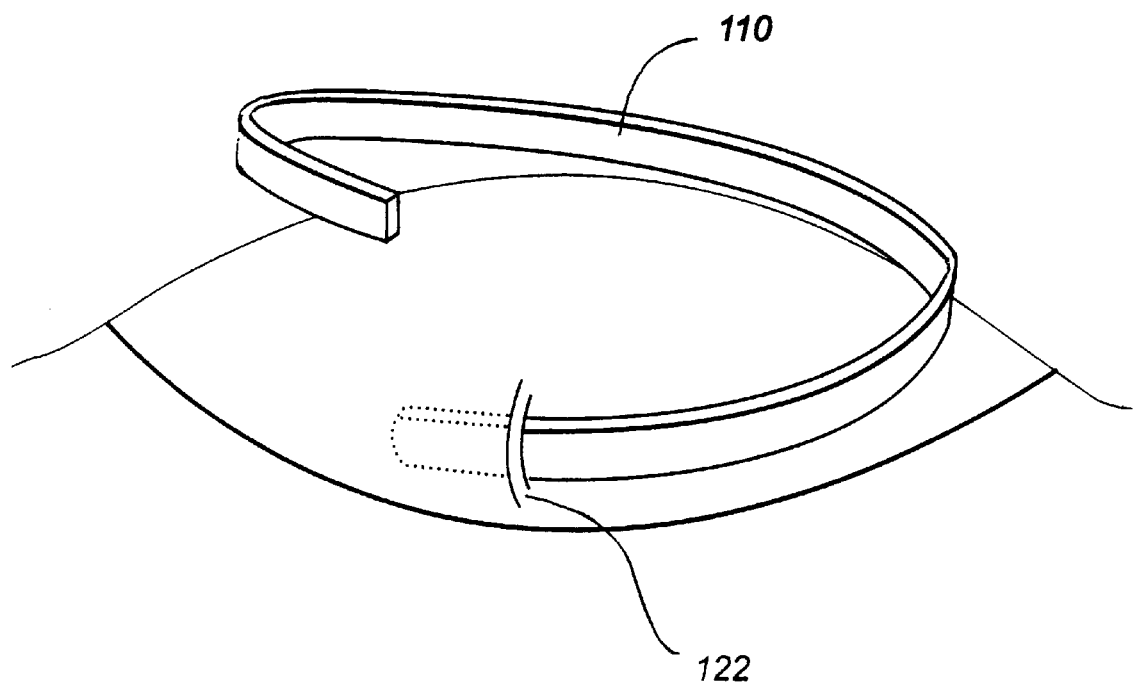

FIG. 10 depicts a technique of implanting the Type "B" implant segment of FIG. 9.

DETAILED DESCRIPTION OF THE INVENTION

The present invention may be described herein as an $MI^3$ system and technique (magnetoresonant induction of intrastromal implant) and is adapted for corncal re-shaping. The $MI^3$ system and technique may be utilized to correct mild to high hyperopia and presbyopia by steepening the anterior corneal curvature in a single treatment, or in periodic treatments over the lifetime of the patient, once the implant is in place. In contrast to other corneal re-shaping procedures (e.g. LASIK and PRK) which are designed for once-in-a-lifetime correction, the disclosed $MI^3$ system and technique is designed as a maintenance therapy that may be repeated annually or even monthly to fine-tune corneal curvature. The $MI^3$ technique will require less than a few minutes of procedure time in an office setting. Such corneal re-shaping with the $MI^3$ system and technique can be accomplished without invasion of the patient's visual axis. The implants are also removable.

The $MI^3$ system comprises a combination of (components including (i) at least one implantable intrastromal element, and (ii) an oscillating magnetic field generator together with a dosimetry control system including at least one emitter body adapted for positioning proximate to the patient's eye and intrastromal implant. Thus, the $MI^3$ system is adapted to deliver thermal effects to appropriate stromal lamellace by non-contact inductive heating of the implant which in turn contracts or compresses stromal collagen fibrils into a circumferential cinch about an anterior layer of the cornea and steepens the anterior corneal curvature. The dosimetry control system controls the power level and duration of exposure of the oscillating magnetic field(s). These components and aspects of the system will be described in order below, and subsequently in their use in performing the method(s) of the invention.

Figure 1A:
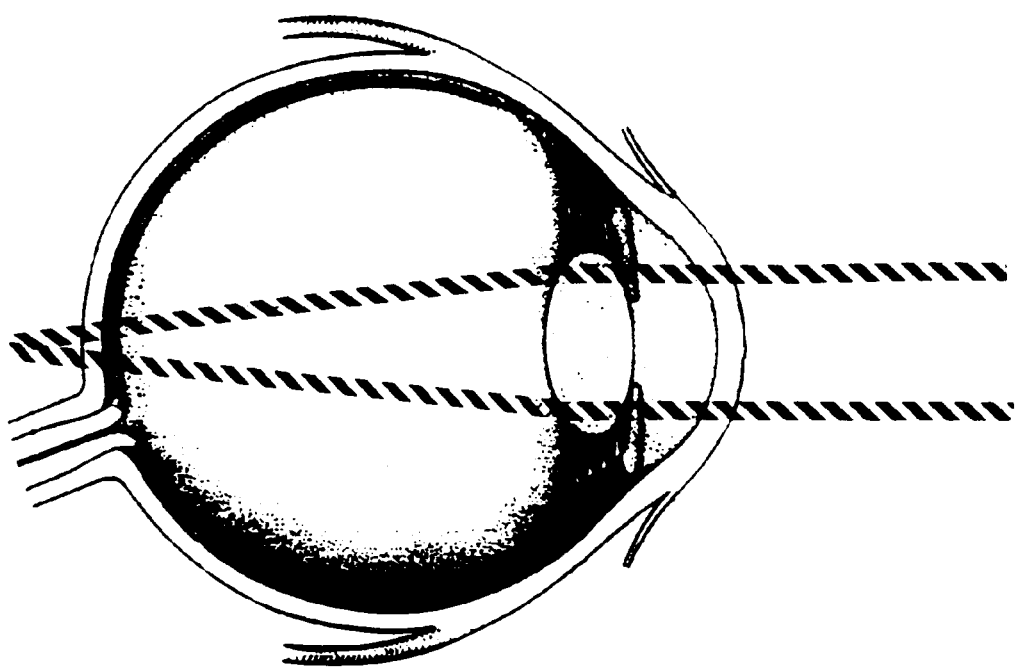
FIG. 1A is a sectional view of a patient's eye which is hyperopic with the focal point of an image being projected beyond the retina.
Figure 1B:
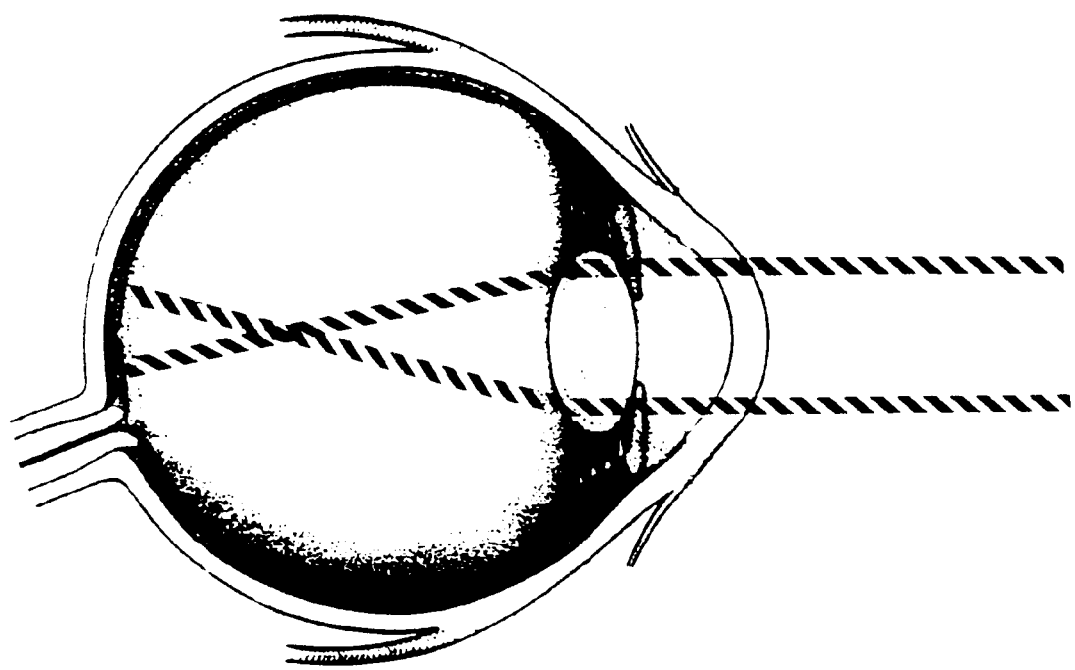
FIG. 1B is a sectional view of a patient's eye which is myopic with the focal point of an image being projected in front of the retina.
Figure 1C:
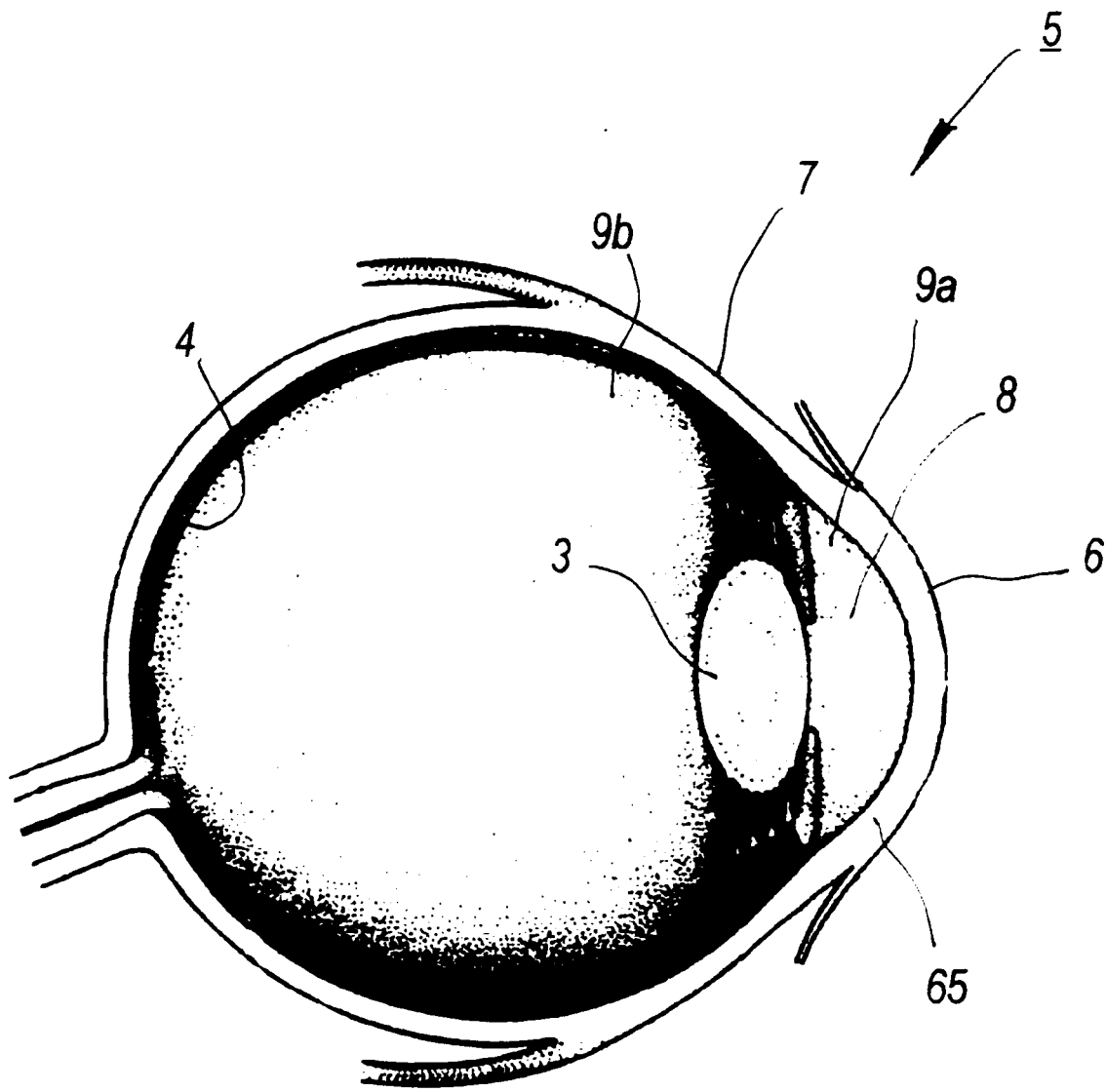
FIG. 1C is a sectional view of a human eye illustrating its anatomy.
Figure 2:
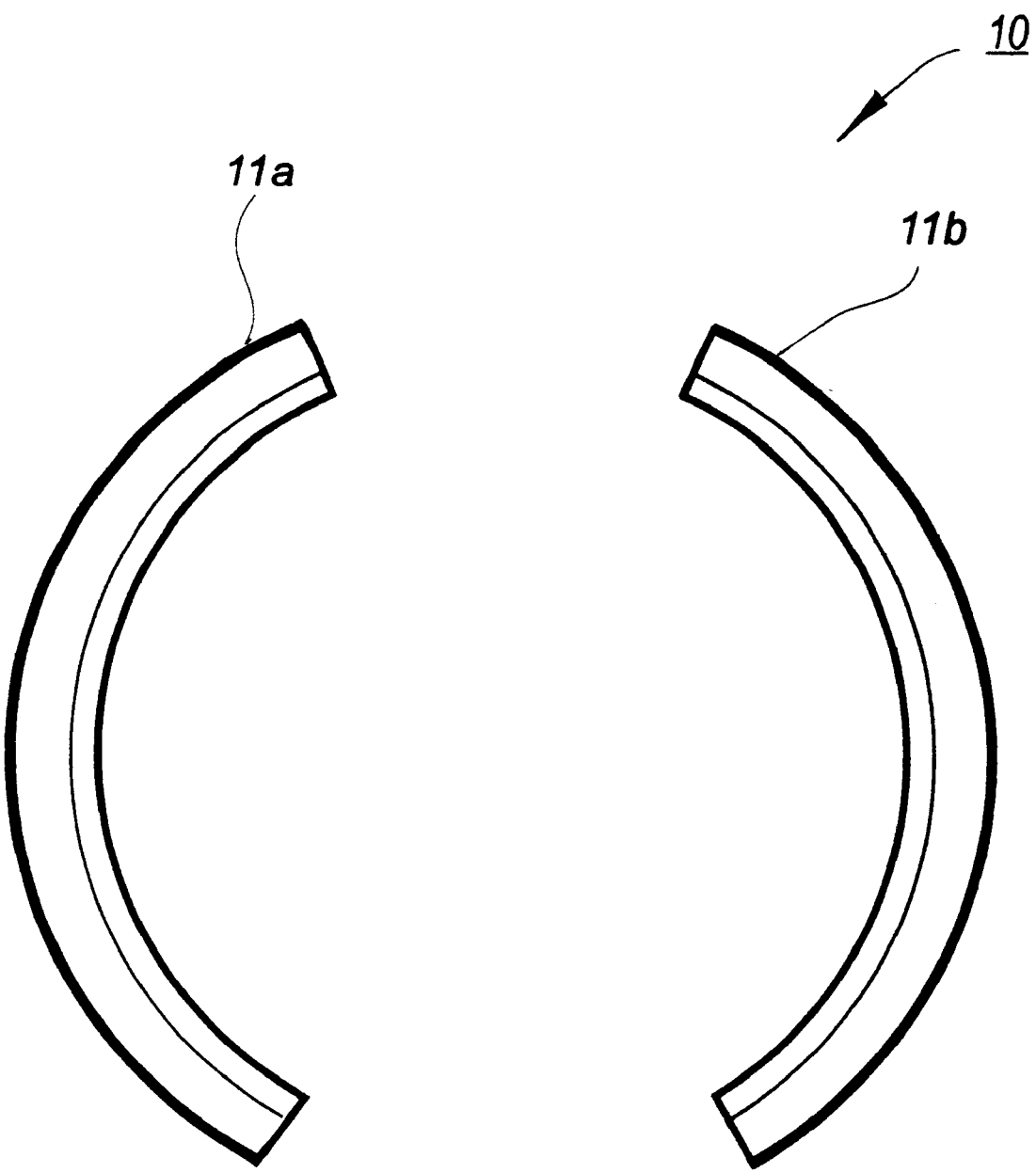
FIG. 2 is a plan view of a Type "A" embodiment of a magnetically responsive intrastromal implant.
Figure 3:
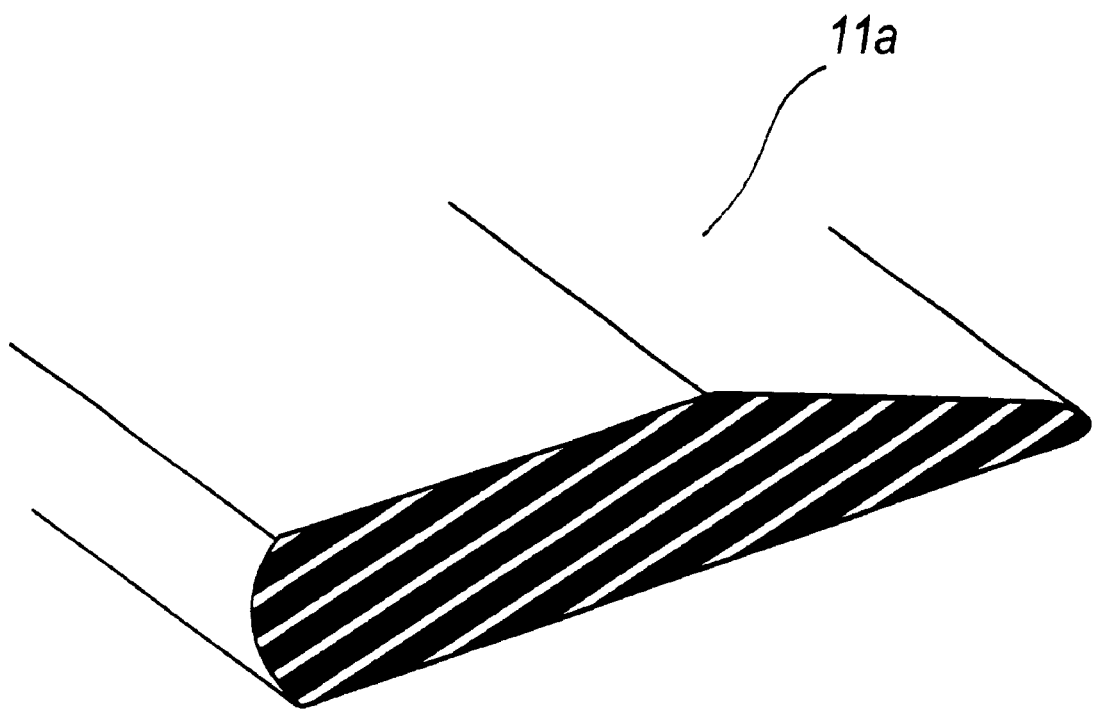
FIG. 3 is a sectional view of the magnetically responsive implant segment of FIG. 3 showing a first preferred cross-sectional shape.
Figure 4A:
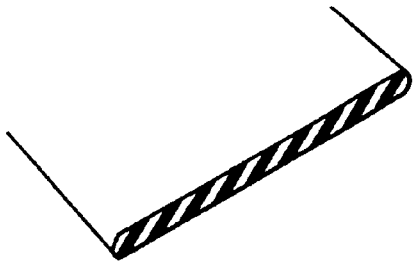
FIGS. 4A–4D are sectional views of other the magnetically responsive segments similar to that of FIG. 3 illustrating alternative cross-sectional shapes.
Figure 4B:
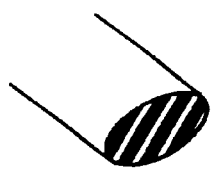
Figure 4C:
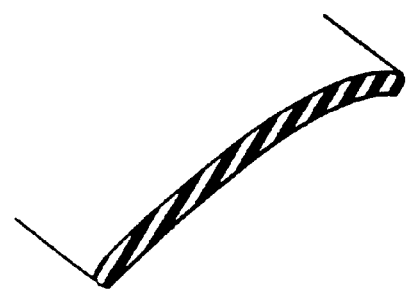
Figure 4D:
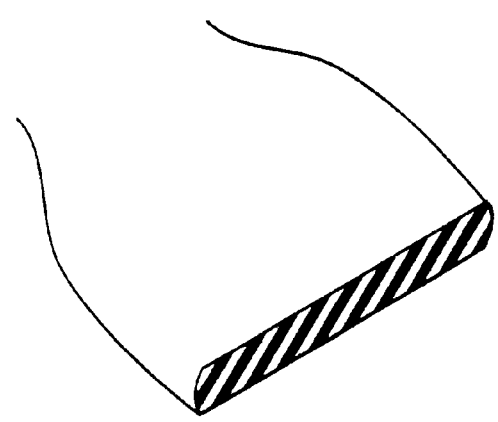

1. Type "A" Magnetoresonant Intrastromal Implant. FIG. 2 illustrates a Type "A" embodiment of magnetoresonant implant 10, or in other words an implant that will thermally respond to non-contact induction of an oscillating magnetic field. Implant 10 (or implant segments, collectively) comprises two arc-shaped segments 11a and 11b having a maximum outer diameter of about 10.0 mm. and minimum inner diameter of about 5.0 mm. In other words, the implants will have a diameter D about an optical axis of a cornea as described below. The angular or radial extension R of each segment is from about 120° to 180°. Referring to FIG. 3, the width W of each implant segments 11a and 11b may range from about 0.02 mm. to about 2.0 mm. and is typically uniform although it may vary as described below. The thickness T of the segments may be from about 0.005 mm. to about 0.05 mm. As can be seen in FIGS. 3 and 4A, the edges 12 and ends 15 of the segment 10 preferably are smoothed or rounded for implantation in the patient's eye as will be described herein. FIGS. 4A–4D depict a range of possible cross-sections of an implant segment 10 that fall within the scope of the invention, for example generally rectangular, oval or round, oblate and/or concave, or flat with a varying width. As shown in FIG. 2, the implant segment is somewhat flexible (see phantom view) but rigid enough for inseition as described below. An objective of the invention is to provide an implant having a cross-section (i.e., width W and thickness T) with sufficient mass to be generate the desired thermal effects when subjected an oscillating magnetic field of a particular strength, while at the same time the implant has a thickness that does not markedly alter post-implantaton corneal curvature due to the implant thickness. For this reason, the preferred implant is one that is substantially thin. The above dimensions are further adapted to allow removal of the implant at a later date. For example, the dimensions of the implant are large enough to allow for easy gripping with a removal tool.

The implant 10 may be formed or molded by any suitable means of any biocompatible material such as medical grade titaniurrm or another metal. All such metallic implants will resonate when subjected to an oscillating magnetic field to provide the thermal effects desired as will be described below in a method of the invention. Implants of a metallic material with minimal dimensions may not be generally visible except on close inspection of the patient's cornea. Such a metallic implant may be colored, cross-striated or patterned to match the patient's iris color or markings to make the implant less visible for cosmetic reasons.

Alternatively, the implant may be of any suitable biocompatible polymeric material that is known in the art, providing the polymeric material will resonate (and thus be frictionally heated by ionic agitation) when subjected to an oscillating magnetic field, and for this reason the polymeric material may be a admixture of polymeric and metallic, magnetic, paramagnetic or superparamagnetic materials. For example, it is believed that a polymeric formulation of polymethyl methactylate together with a biocompatible metallic powder can be molded into an implant to provide a substantially transparent or translucent implant (for cosmetic reasons) while at the same time providing an implant highly sensitive to resonance in an oscillating magnetic field.

Figure 5:
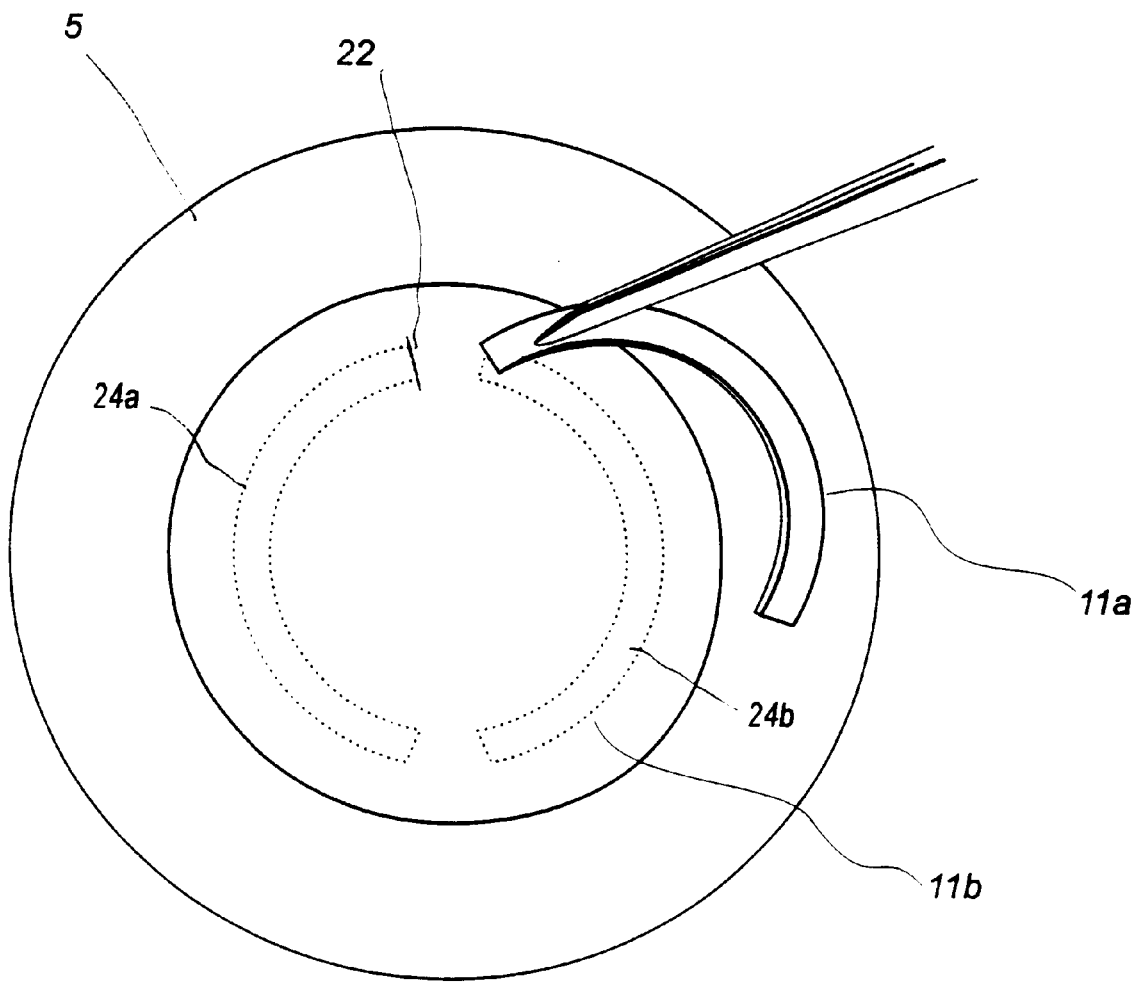
FIG. 5 depicts a technique of implanting the Type "A" implant segments of FIG. 3.

Referring now to FIG. 5, the surgical tecinique for implanting segments 11a and 11b is shown. The implantation surgery can be done witli topical anesthesia alone, local anesthesia alone, topical anesthesia in combination with short-acting sedation, or topical anesthesia with intravenous conscious sedation. For example, a povidone-iodine solution (2.5 percent) may be applied to the cul-de-sac and left for about two minutes, and then rinsed away with a balanced salt solution. The patient is draped and prepared as is typical for any anterior segment surgery. The surgeon places a 6 mm. to 12 mm. optical zone marker with cross-hairs over the geometric center of eye 5 and the cornea 6. The marker is pressed on the anterior corneal surface so that the cross-hairs make an indentation at the optical or visual axis 15 of the cornea, which mark may be enhanced with a dye or marking pen. A segment placement line is marked with gentian violet on the corneal surface at the appropriate diameter, which overlies channels that are to be bluntly dissected to receive the implants. A mark also is made for a radial incision 22 which may be either at 0° as shown in FIG. 5 (a superior location) or at 180° (an inferior location). A diamond knife with depth-adjustable blade is set to a predetermined depth ranging from about 50 microns to about 250 microns. The depth measurement is based on the desired depth of intrastromal channels, and is generally in the anterior stroma just below the Bowman's membrane or in the mid-anterior stroma for reasons described below. The depth of the channel also is made with reference to pre-operative corneal pachymnetry (corneal thickness), for example with an Orb- scan topography and pachymetry system available from Orbtek Inc., 3030 Main Street, Suite 600, Salt Lake City, Utah.

The corneal tissue at the base of radial incision 22 may be separated laterally with a modified stromal spreader as is known in the art to prepare a segment-receiving channel on either side of incision 22. The surgeon then may place a vacuum centering guide about the mark at the central cornea. Thereafter, the surgeon inserts an arc-shaped dissector into the radial incision and bluntly dissects channels 24a and 24b in the clockwise and counter-clockwise directions from incision 22. The vacuum device then is removed. The surgeon then may insert the intrastromal implant segments into the channels 24a and 24b. The radial incision may be closed with interrupted 10-0 nylon sutures. After the cornea has healed, the patient will be ready for later treatments with the $MI^3$ system and technique.

Figure 6:
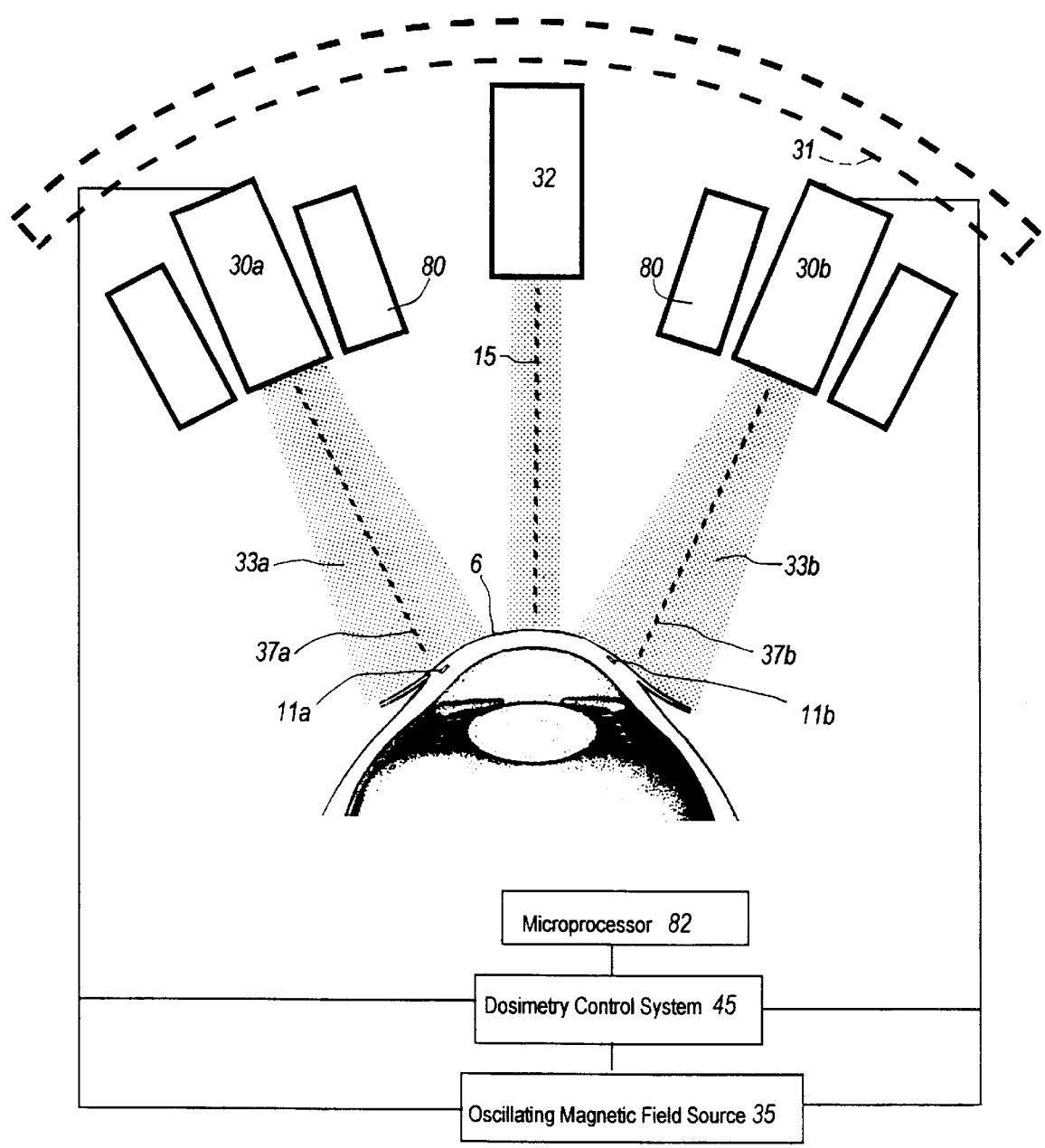
FIG. 6 is a schematic sectional view of a plurality of magnetic field emitters of the present invention shown in relation to the patient' cornea.

2. Oscillating Magnetic Field Application System. FIG. 6 schematically illustrates the $MI^3$ system components in conjunction with a slit lamp (viewed from above) which includes an applicator array or magnetic field emitter array 30, having individual emitters 30a and 30b that are adapted to be positioned proximate to a patient's cornea 6. For example, emitters 30a and 30b typically would be mounted a support structure 31 attached to the slit lamp's magnification box indicated at 32 such as in a Zeiss Model SL-130 available from Humphrey Instruments, Inc., San Leandro, Calif. 94577. Thus, the physician operating the $MI^3$ system may utilize the biomicroscope to simultaneously view the performance of the method. It should be appreciated that the number (N) of emitters may range between one and about six (N=1 to 6) and be angularly spaced in opposition around optical axis 15 of eye 5 and fall within the scope of the invention. Preferably, the number N of emitters is from 1 to 4. The preferred embodiment is shown with two emitters 30a and 30b that may be adjusted (see arrows 32) in relation to eye 5 by any suitable adjustable arm means. The off-axis positioning of the emitters provides an open cylindrical treatment corridor 40 from about 5 mm. to 20 mm. in diameter around axis 15 of eye 5 (see FIG. 6). More particularly, corridor 40 is free from physical interference from emitters 30a and, 30b allowing one or more light beams from a slit lamp, corneal topographic apparatus, or other ophthalmic diagnostic or treatment device to be used concurrently with the $MI^3$ system's treatment of cornea 6 prior to, during and after the performance of the method disclosed herein for re-shaping corneal curvature.

FIG. 6 shows emitters 30a–30b each emitting a separate oscillating magnetic field (or induction field) as indicated by field patterns 33a and 33b. Each emitter is operatively connected to oscillating magnetic field source 35 that projects fields 33a and 33b generally outward about an emitter axis (37a–37b) toward a quadrant of eye 5 that carries an implant segment 11a or 11b. The plurality of emitters and their symmetrical arrangement in opposition to one another relates to an important aspect of a method of the invention wherein inductive resonance of an individual implant segment may be (i) nonsimultaneous with another; (ii) simultaneous with another for symmetry of treatment; (iii) varied in inductive field power levels between spaced-apart implant segments; or (iv) the oscillating fields may be varied in phase to alter the affects of energy delivery. Generally, the emitters are adapted to provide a symmetry and simultaneity of treatment relative to optical axis 15. It is understood that the oscillating magnetic field of each emitter will cause resonant effects in more than a single implanted segment, but it is believed that individual emitters spaced apart and positioned close to the anterior corneal surface just above the radius of the implant will allow for varying energy levels at any particular spaced-apart implant segment.

The block diagram of FIG. 6 furter shows closimetry control system 45 that is adapted to control power delivery which will be described below in its use during the performance of the technique of the invention.

3. Techniques of Use of MI³ System. Turning now to FIGS. 7A–7B & FIG. 8A, a sequence of partial sectional views of cornea 6 are shown indicating the manner of utilizing the combination of the intrastromal implant 10 and emitter array 30 to steepen the anterior corneal curvature in a periodic treatment for hyperopia or presbyopia.

FIG. 7A shows the cornea with implant segments 11a and 11b in place with the pre-treatment anterior corneal surface indicated at AC. Following corneal topographic measurements and diagnoses, assume that the ophthalmologist determines that corneal curvature should be approximately as indicated at the dashed line AC'.

Referring now to FIG. 8A, an enlarged sectional view of the implant 11a is shown in relation to layers of cornea 6. FIG. 8A shows that cornea 6 comprises a number of distinct layers which together total a corneal thickness ranging from about 500 to 650 microns at the center and from 1000 to 1200 microns at its periphery (at a diameter from 12 mm. to 15 mm. around axis 15). FIG. 8A shows epithelium 50 which is several cells thick and is smooth and comprises the clear outer surface of the eye that is exposed to the environment. A tear film (not shown) covers the epithelium. The epithelium 50 has a thickness of about 50 microns. Beneath the epithelium is a basal membrane 52 (or basement membrane of epithelium). The Bowman's membrane 60 is from 15 to 20 microns thick and plays a significant role in the morphology of the cornea. The Bowman's membrane is a cellular and comprised of collagen fibrils of varying diameter which provide significant tensile strength to the cornea and forms a containment shell to contain stromal lamellae 62 any resist intraocular pressure (IOP) of aqueous humor 9a in anterior chamber 8. In implementing any refractive corrective strategy, it is considered important to preserve the basement membrane and Bowman's membrane, 52 and 60, substantially intact. Any damage to the epithelium will be quickly corrected by epithelial cellular regeneration produced by cells in the basement membrane 52. Any significant damage to, or removal or ablation of, the Bowman's layer 60 (e.g., in PRK) is undesirable since that layer will not regenerate.

The stroma 65 comprises up to 90 percent of the corneal thickness. FIG. 8A shows that stroma 65 is comprised of up to 500 thin layered sheets or lamellae 62 with each layer containing collagen fibrils 66 surrounded by a mucopolysaccharide (MPS) and glycoprotein matrix, collectively called GAGs or ground substance 67 herein. Interleaved between the lamellae 62 are keratocyte layers 70, the constitutive cell of the stroma which synthesize the collagen molecules and the GAGs 67. It is an important objective of the method of the invention to elevate temperature levels in lamellae 62 (and collagen fibrils) in proximity to implant 10 to cause longitudinal contraction of collagen molecules and fibris 66 without excessive death of keratocytes, for any excess cell death could stimulate a stronger inflammatory or wound healing response than would be desirable. Beneath stroma 65 are two other layers: Descemet's membrane 73 and the endothelium 75. Descemet's membrane has a thickness of about 7 microns and endothelial layer 75 comprises a single layer of cells having a thickness of about five microns. It is important that the endothelium 75 not be damaged since it will not regenerate. It is for this reason that implant 10 is placed in the anterior or mid-anterior stroma, thus preventing heat transfer to the endothelium.

As shown in FIGS. 7A & 8A, the location of implant 10 is generally just below Bowman's layer 60 and within the anterior or mid-anterior portion of stroma 65. Since the Bowman's layer is without keratocytes and forms a strong containment or shell around the stroma 65, it is believed that contraction of collagen fibrils 66 to form the desired circumferential cinch C about the cornea is best focused on the Bowman's layer and the stromal layers just below the Bowman's layer.

FIG. 7B shows the oscillating magnetic fields 33a and 33b being applied via emitters 30a and 30b which resonate the implant segments 11a and 11b until the temperature of the implant preferably reaches between 55° C. and 85° C. which increases the temperature of collagen fibrils 66 in close proximity to the implant to a similar temperature. This temperature elevation in turn causes longitudinal contraction of such collagen fibrils. More preferably, the inductive method elevates the temperature of the implant and proximate collagen fibrils to between 60° C. and 80° C. Still more preferably, the inductive method elevates the temperature of the implant and proximate collagen fibrils to between 65° C. and 70° C. The longitudinal contraction of the fibrils causes the circumferential cinch indicated at C around the cornea at diameter D about axis 15 which thus will re-shape or steepen the anterior cornea to the desired shape indicated as AC'. The magnetic field may range between about 1,000 and 25,000 Gauss, and preferably is between about 10,000 and 15,000 Gauss (not limiting). The rate of oscillating the magnetic field may range between about 1,000 Hz. and 50,000 Hz (not limiting).

Turning now to FIG. 8B, the enlarged sectional view of cornea 6 and implant segment 11a indicates a region 90 around the implant in which collagen fibrils have been longitudinally contracted thus causing the circumferential cinching effect.

4. Dosimetry Control for of MI³ System. The MI³ system includes a dosimetry control system indicated at 45 in FIG. 6 that is adapted to control the timing and the power level of oscillating magnetic field energy delivery through emitters 30a–30b in various operational modes. The dosimetry control system can operate in a basic mode of operation wherein a pre-set program is used to control the (i) power level, and (ii) duration of energy delivery from source 35.

Other operational modes that are preferred relate to feedback-controlled modes based on signals from detector systems or sensors 80 (collectively) as shown in FIG. 6. In a first feedback controlled mode, radiometric surface temperature at the anterior corneal surface AC may be monitored with sensor 80, e.g., a 1 mm.² liquid $N_2$ cooled HgCdTe infrared (IR) detector with a focal plane from about 10 mm. to 200 mm. from anterior surface AC of cornea 6. The IR detector element may be optically filtered as is known in the art with an appropriate bandpass filter. The detecticon system further may be configured with collection optics to allow the detector to detect peak surface temperatures in any treatment zones overlying an implant segment. Alternatively, there may be a plurality of such IR detectors with an individual detector for each treatment zone, or on detector covering two zones etc. Such a IR detector may be a Model MDD-10-EO-S1 from Cincinnati Electronics, Inc., Mason, Ohio. In this type of feed-back controlled mode, the dosimetry control system 45 may terminate magnetic field energy delivery upon detected surface temperature reaching a pre-set, for example any temperature between 55° C. and 85° C. The detected temperature of anterior surface layers of the cornea is predictive of temperatures at or within the Bowman's layer 60 or stroma 65 by means of biological thermal modeling.

In another feedback-controlled operatioral mode, the dosimetry control system 45, which typically includes microprocessor 82 together with an appropriate software program, can be designed to modulate power levels of the magnetic field energy delivery at any level among a continuous range of power levels at the emitters 30a–30b. For example, each zone may have an IR detector directed toward it that is adapted to modulate power in that zone with the objective of maintaining a particular suriface temperature, or turning the power off at a high limit and turning power on again at a low limit temperature.

In another preferred feedback-controlled operational mode, the dosimetry control system 45 can be designed to modulate power levels of the magnetic field energy delivery at any levels at the emitters 30a–30b based on changes in corneal topographic data intraoperatively. For example, a corneal topography system such as the Orbscan system by Orbtek, Inc. (described above) may be integrated into the system where the Orbscan off-axis CCD's (indicated at 85 in FIG. 6) are adapted to continuously monitor changes in corneal curvature. When the software program determines that an optimal corneal curvature is achieved, then the program is adapted to modulate power or terminate power delivery in a particular zone or in all zones of the eye.

The software that is part of the dosimetry control system, as the term is used herein, includes a conventional software program, a program within a programmable chip, or any other form of algorithm carried in any form of memory storage system. Within the hardware portion of dosimetry control system 45, there may be a keyboard, disk drive or other non-volatile memory system, displays as are well known ill the art for operating such a system.

The feedback-control components of the dosimetry control system described above is based on signals from an IR detector or from a corneal topography system. It should be appreciated that the feedback control or modulation of photonic energy delivery may be based on several other optical or other detection modalities that may be utilized to insure that excess energy is not delivered to prevent over corrections of corneal curvature. It should be appreciated that such alternative detection systems are within the scope of the present invention and include: (i) using secondary light emitters and sensor systems for polarization-sensitive optical coherence tomographic (PS-OCT) signaling to insure that birefringence alternations do not occur, or occur to the desired degree, in stromal tissue which alterations are precursors to tissue denaturation; (ii) using secondary light emitters and sensing systems for diffusing-wave spectroscopic methods of tissue characterization; (ii) using secondary light emitters and sensors for two-photon fluorescence imagng and other forms of fluorescence sensing; (iii) using secondary light emitters and sensing systems for time-gated imaging using snake-like photons; or (iv) using secondary light emitters and sensing systems for general OCT methods.

5. Type "B" Magnetoresonant Intrastromal Implant. FIG. 9 depicts another implant 110 that is similar to the Type "A" embodiment except that it is one piece. Alternatively, such an embodiment may have different densities of resonant material formed into a molded polymeric implant. For example, portion 112a may be more sensitive to an oscillating magnetic field than portion 112b or 112c. Thus, the system may be adapted for a single level energy developing different temperatures at various locations which would be useful in treatment of recurrent astigmatism. FIG. 10 depicts the technique of implanting the implant 110 througl radial incision 122.

In another method of utilizing the $MI^3$ system, it should be appreciated that all of the above-described methods could additionally utilize a (contact lens as a heat sink (not shown). The contact lens could be made of any material such as sapphire, quartz of plastic as is known in the art. The effect of such a heat sink contact lens would be to cool the anterior surface and underlying layers of cornea 6 during the resonance of the implant segments which would maintain epithelium 50 at a lower temperature than otherwise might be the case. More preferably, the contact lens could be cooled by any suitable means, (e.g., pre-cooling to 0° C. to 20° C. in a freezer) prior to treatment which would likely reduce the death of keratocytes in the cornea and possibly limit corneal shape-changing effects that result from the wound healing response. (In the use of such a contact lens, the IR detector system described above would not be used).

It should be appreciated that the invention can be generalized for localizing thermal effects in tissue in the interior of a patient's body by the uses of a non-contact magnetoresonant system or combination described above. For example, a magnetoresonant intraluminal prosthesis or stent (not shown) can be implanted in the lumen of a patient's blood vessel (or other tubular anatomic structure) following a balloon angioplasty or other similar procedure in any coronary or other peripheral vascular procedure where intraluminal prostheses or stents are commonly used. Such a magnetoresonant prosthesis then may be inductively (or magnetoresonantly) elevated in temperature at the time of implantation or more logically in a periodic treatment over time to cause various therapeutic effects. In such an early post-implantation treatment, the temperature elevition of the prosthesis may work as an thrombolytic therapy. In one or more later post-implantation treatments, the temperature elevation of the prosthesis may be used as a treatment against restenosis by elevating the temperature of the vessel wall portion (cells) underlying the overgrowth of intima. Such therapy will damage the cells to prevent proliferation of such cells underlying the intima which are often the cause of restenosis or in-stent restenosis. For this reason, the magnetoresonant prosthesis should have as much mass as feasible to deliver the necessary level of thermal effects (cell damage or death) to the tissue surrounding the implant. The system may further include an magnetoresonant emitter that is small enough to be carried and attached to the body surface overlying the implant, including a battery and timer or processor to provide magnetoresonant energy and timing to inductively heat the implant.

Specific features of the invention are shown in some drawings and not in others, and this is for convenience only and any feature may be combined with another in accordance with the invention. Further variations will be apparent to one skilled in the art in light of this disclosure and are intended to fall within the scope of the appended claims.

What is claimed is:

1. A combination system for delivering energy to a body structure at a selected location in the interior of a patient's body for therapeutic purposes, comprising:

an electromagnetic field responsive implantable composition for implantation at said selected location at the interior of the patient's body; and an electromagnetic field emitter;

wherein said emitter is capable of generating an oscillating electromagnetic field at a selected strength and for a selected duration to resonate the implantable composition thereby delivering energy to said selected location;

a controller for controlling the timing and/or power level of the electromagnetic field generated by said emitter; and a feedback control system for signaling said controller for controlling the timing and/or power level of the field generated by said emitter.

2. The system of claim 1 wherein the feedback control system comprises an infrared sensor for detecting a body surface temperature overlying the selected location.

3. The system of claim 1 wherein the feedback control system comprises a topographic sensor for detecting changes in the topography of a body surface overlying the selected location.

4. A method for altering the curvature of a human cornea for refractive purposes, comprising:
(a) implanting an electromagnetic field responsive composition in a patient's cornea;
(b) positioning an electromagnetic field emitter at an exterior of the patient's cornea; and
(c) generating an oscillating eleciromagnetic field with said emitter at a selected strength and for a selected duration for resonating said responsive composition to thereby achieve a selected elevated temperature therein;
(d) wherein step (c) alters the molecular structure of proteins proximate to the responsive composition by thermal means thereby altering cornea curvature.

5. The method of claim 4 wherein the selected elevated temperature of the responsive composition causes longitudinal contraction of collagen in the cornea.

6. A method of delivering energy to a body structure at an interior of a patient's body for therapeutic purposes, comprising the steps of:
(a) implanting at least one electromagnetic field responsive composition at a selected location in the body structure in the interior of the patient's body;
(b) positioning an electromagnetic field emitter within a range of the responsive composition in the patient's body; and
(c) generating an oscillating electromagnetic field with said emitter at a selected strength and for a selected duration thereby resonating said responsive composition;
(d) wherein the resonation of the responsive composition thereby delivers energy to provide a thrombolytic therapy to the selected location.

7. A method of delivering energy to a body structure at an interior of a patient's body for therapeutic purposes, comprising the steps of:
(a) implanting at least one electromagnetic field responsive composition at a selected location in the body structure in the interior of the patient's body;
(b) positioning an electromagnetic field emitter within a range of the responsive composition in the patient's body; and
(c) generating an oscillating electromagnetic field with said emitter at a selected strength and for a selected duration thereby resonating said responsive composition;
(d) wherein the resonation of the responsive composition thereby delivers energy to the selected location; and (e) wherein step (c) is preceded by the further step of placing a heat sink device at a body surface overlying said selected location to cool body surface layers while elevating the temperature at the selected location.

8. A method of delivering energy to a body structure at an interior of a patient's body for therapeutic purposes, comprising the steps of:
(a) implanting at least one electromagnetic field responsive composition at a selected location in the body structure in the interior of the patent's body;
(b) positioning an electromagnetic field emitter within a range of the responsive composition in the patient's body; and
(c) generating an oscillating electromagnetic field with said emitter at a selected strength and for a selected duration thereby resonating said responsive composition and elevated in the temperature of the responsive composition to teIC range of about 55° C. to 85° C.;
(d) wherein the resonation of the responsive composition thereby delivers energy to the selected location and the elevated temperature of the responsive composition causes longitudinal contraction of collagen proximate thereto.

9. A method of delivering energy to a body structure at an interior of a patient's body for therapeutic purposes, comprising the steps of:
(a) implanting at least one electromagnetic field responsive composition at a selected location in the body structure in the interior of the patient's body;
(b) positioning an electromagnetic field emitter within a range of the responsive composition in the patient's body; and
(c) generating an oscillating electromag etic field with said emitter at a selected strength and for a selected duration thereby resonating said responsive composition;
(d) wherein the resonation of the responsive composition thereby delivers energy to the selected location and the responsive composition is implanted in a patient's cornea.

10. A method of delivering energy to a body structure at an interior of a patient's body for therapeutic purposes, comprising the steps of:
(a) implanting at least one electromrtagnetic field responsive composition at a selected location in the body structure in the interior of the patient's body;
(b) positioning an electromagnetic field emitter within a range of the responsive composition in the patient's body; and
(c) generating an oscillating electromagnetic field with said emitter at a selected strength and for a selected duration thereby resonating said responsive composition;
(d) wherein the resonation of the responsive composition thereby delivers energy to the selected location and the responsive composition is implanted in a tubular anatomic structure in a patient's body.

11. A method of delivering energy to a body structure at an interior of a patient's body for therapeutic purposes, comprising the steps of:
(a) implanting at least one electromagnetic field responsive composition at a selected location in the body structure in the interior of the patient's body;
(b) positioning an electromagnetic field emitter within a range of the responsive composition in the patient's body; and (c) generating an oscillating electromagnetic field with said emitter at a selected strength and for a selected duration thereby resonating said responsive composition;

(d) wherein the resonation of the responsive composition thereby delivers energy to the selected location and the responsive composition is implanted in a blood vessel in a patient's body.

12. A method of delivering energy to a body structure at an interior of a patient's body for therapeutic purposes, comprising the steps of:

(a) implanting at least one electromagnetic field responsive composition at a selected location in the patient's eye;

(b) positioning an electromagnetic field emitter within a range of the responsive composition in the patient's eye; and (c) generating an oscillating electromagnetic field with said emitter at a selected strength and for a selected duration thereby resonating said responsive composition;

(d) wherein the resonation of the responsive composition thereby delivers energy to the selected location the patient's eye.

13. A method of delivering energy to a body structure at an interior of a patient's body for therapeutic purposes, comprising the steps of:

(a) implanting at least one electromagnutic field responsive implant within a tubular anatomic structure in a patient's body;

(b) positioning an electromagnetic field emitter within a range of the implant in the patient's body; and (c) generating an electromagnetic field with said emitter at a selected strength and for a selected duration which is received by said implant;

(d) said implant thereby delivering energy to the selected location across an interface between the implant and the tubular anatomic structure.

* * * * *